(12) United States Patent
Binder et al.

(10) Patent No.: US 7,544,718 B2
(45) Date of Patent: Jun. 9, 2009

(54) PROCESS FOR THE PREPARATION OF AN EMULSION

(75) Inventors: Wolfgang Binder, Hamburg (DE); Angel Montero Martínez, Madrid (ES); Ramon Rodriguez Nunez, Madrid (ES)

(73) Assignee: Beiersdorf AG, Hamburg (DE)

( * ) Notice: Subject to any disclaimer, the term of this patent is extended or adjusted under 35 U.S.C. 154(b) by 781 days.

(21) Appl. No.: 10/928,531

(22) Filed: Aug. 26, 2004

(65) Prior Publication Data

US 2005/0058680 A1 Mar. 17, 2005

Related U.S. Application Data

(63) Continuation of application No. PCT/EP03/01885, filed on Feb. 25, 2003.

(30) Foreign Application Priority Data

Feb. 26, 2002 (DE) .................. 102 08 265

(51) Int. Cl.
*A61K 8/06* (2006.01)
(52) U.S. Cl. .................. 514/937; 514/782; 514/783; 514/983; 424/401
(58) Field of Classification Search .......... 514/772.3, 514/782, 783, 983
See application file for complete search history.

(56) References Cited

U.S. PATENT DOCUMENTS

| 4,446,127 | A | 5/1984 | Bucheler et al. |
| 5,075,113 | A | 12/1991 | DuBois |
| 5,811,112 | A * | 9/1998 | Chandar et al. ............. 424/401 |
| 5,958,495 | A | 9/1999 | Klinksiek |
| 6,468,578 | B1 | 10/2002 | Bodor et al. |
| 6,537,562 | B1 | 3/2003 | Boettcher et al. |

FOREIGN PATENT DOCUMENTS

| DE | 391 98 28 A1 | 12/1990 |
| DE | 199 11 777 A1 | 9/2000 |
| DE | 199 23 785 A1 | 11/2000 |
| GB | 1 537 112 A | 12/1978 |
| WO | WO 98/32413 A | 7/1998 |
| WO | WO 99/49738 A | 10/1999 |

OTHER PUBLICATIONS

Eine aniage zum kontinuierlichen emulgieren, J. Verfahrenstechnik, 1986, vol. 1-2.*
International Search Report from corresponding International Application No. PCT/EP/01885, dated Dec. 11, 2003.
German Search Report from corresponding German Application No. 102 08 265.0, dated Oct. 21, 2002.

* cited by examiner

*Primary Examiner*—Gina C. Yu
(74) *Attorney, Agent, or Firm*—Greenblum & Bernstein, P.L.C.

(57) ABSTRACT

The invention is a continuous process for preparing a cosmetic or dermatological preparation, comprising emulsifying at least two pre-products in at least one mixing apparatus, cooling the emulsion to less than 40° C. by adding an aqueous phase with a lower temperature than the mixture, adding at least one ingredient selected from the group consisting of perfume oil and temperature-sensitive active ingredients, and homogenizing the emulsion in at least one homogenizing apparatus at a temperature of from 20 to 50° C. The invention also includes a product made by such process.

25 Claims, 1 Drawing Sheet

PROCESS FOR THE PREPARATION OF AN EMULSION

CROSS-REFERENCE TO RELATED APPLICATIONS

This is a continuation application of PCT/EP03/01885, filed Feb. 25, 2003, which is incorporated herein by reference in its entirety, and also claims the benefit of German Priority Application No. 102 08 265.0, filed Feb. 26, 2002.

FIELD OF THE INVENTION

The present invention relates to a process for the preparation of cosmetic or dermatological preparations, in particular of preparations comprising emulsions, PIT emulsions and washing-active substances.

BACKGROUND OF THE INVENTION

Cosmetic or dermatological preparations in the form of emulsions, PIT emulsions and preparations comprising washing-active substances are widespread. Emulsions may be W/O or O/W emulsions or else multiple emulsions, i.e. emulsions containing more than two phases. They are sold in the form of creams, lotions, but also as perspiration-inhibiting, body-odour-reducing cleansing and sunscreen preparations. PIT emulsions are particular forms of emulsions. They are characterized by the method of their preparation and the droplet sizes resulting therefrom. For the preparation, emulsifiers or emulsifier systems are used which change their polarity depending on the temperature, meaning that phase inversion arises during the preparation. As a result of this phase inversion, particular product properties are achieved, such as, for example, a particular optical appearance or an extraordinarily low viscosity. Such preparations are suitable, for example, as sprayable skincare or sunscreen emulsions. Finally, preparations comprising washing-active substances are used as body- or hair-cleansing compositions, and also as dishwashing detergents.

Usually, such preparations are prepared in a batchwise process, mostly in a mixer into which the starting substances are introduced and the intermediate or end product are removed after a certain operating time. In this process, all of the process steps which are required for the preparation of the product take place in this one apparatus one after the other: metering, mixing, heating/cooling, emulsifying, cooling. Often, upon removing the product, the product is subjected to subsequent homogenization. Although in food technology continuous plants for the preparation of emulsions such as yoghurt or mayonnaise are widespread, cosmetic or dermatological preparations are only prepared continuously in exceptional cases. This is because the requirements on the stability of cosmetic products are much higher and, due to their more complex composition comprising numerous different components, said products are much more difficult to prepare in stable form. Thus, for example, for a yoghurt, a stability in the region of a few weeks is expected, whereas cosmetic emulsions should be stable over at least 30 months.

Plants which are operated in batchwise processes have a series of disadvantages besides the advantageous flexibility with regard to the products which can be prepared. The long batch times required lead to increased production costs. There is a risk of contamination since the plants have to be emptied and charged frequently. The risk of contamination can be limited by keeping the product temperatures low. This is achieved by using cold aqueous phases. Alternatively, a heat exchanger can also be connected downstream. In most cases, relatively large amounts of air are introduced into the system, which is undesirable.

Known continuous processes are characterized in that the individual phases are metered into a high-performance emulsifying device at the same time. The emulsification and homogenization operation takes place therein with a high input of energy, giving rise to high shear forces. However, the occurrence of high shear forces is able to damage polymers present in the preparations. As a result of simultaneously metering all of the components, they are subjected to relatively high temperatures over prolonged periods. As a result, the use of temperature-sensitive substances is only possible to a limited degree. Such substances are, for example, cosmetic active and functional ingredients, such as fragrances, vitamins, coenzymes, peptides, enzymes, nucleic acids, plant extracts, preservatives, such as, for example, those from 1,2-dibromo-2,4-dicyanobutane and 2-phenoxyethanol.

Although continuous plants with which it is possible to prepare a large number of different cosmetic and/or dermatological preparations are desired, they are not known to date. In particular, a plant with which it would be possible to prepare both low-viscosity emulsions, lotions, creams and body- and hair-cleansing preparations and also dishwashing detergents would represent a significant improvement in the prior art.

It has hitherto not been possible to prepare PIT emulsions in continuous processes since the droplets remain too large despite a high input of energy. Continuously prepared creams and liquid emulsions were in most cases insufficiently stable. During the preparation of preparations comprising washing-active substances, the use of continuous processes in most cases leads to inhomogeneities arising as a result of inadequate mixing. Transparent preparations are therefore only obtainable with difficulty since such inhomogeneities often lead to clouding. For the preparation of O/W emulsions, continuous processes have hitherto not been able to penetrate the market since it has not been possible to achieve products of high quality: in most cases the emulsions were not stable or tended towards oil losses. The cause of this behaviour is assumed to be the fact that homogeneous droplet size distributions cannot be achieved through the use of static mixers on their own.

The article "Eine Anlage zum kontinuierlichen Emulgieren" [A continuous emulsification plant] in the Journal Verfahrenstechnik, volume 1-2 from 1986 describes, for example, a continuous preparation process for the preparation of W/O and O/W creams. The discontinuously prepared pre-products pass through a metering system, a dynamic mixer and a static mixer. Here, a hot/cold process is realized in which the preproducts enter the process in cold or hot form. The emulsion is produced in the dynamic mixer, homogenization takes place in the static mixer, as a result of which the particle size distribution is adjusted. This plant is suitable for the preparation of skin creams, body lotions, mayonnaise and sauces.

In this process, the homogenization operation takes place at 40 to 75° C., although it would be desirable to carry out this step at low temperatures since temperature-sensitive constituents of the formulations, such as odour or aroma substances or active ingredients such as vitamins, should as far as possible not be subjected to thermal stress.

SUMMARY OF THE INVENTION

Starting from this, it was an object of the present invention to find a process which overcomes the disadvantages of the prior art.

It has been found, in a manner unforseen by the person skilled in the art, that a continuous preparation process, as shown in FIG. 1, for cosmetic or dermatological preparations which comprise temperature-sensitive ingredients characterized by a sequence of the following process steps
(a) emulsification in mixing apparatuses (11),
(b) establishing a mixture temperature of less than 40° C. by adding (B) aqueous phase with a lower temperature compared with the mixture,
(c) addition (C) of perfume oil and/or temperature-sensitive active ingredients,
(d) homogenization in apparatuses (13) in the temperature range from 20 to 50° C., particularly preferably 28 to 40° C., overcomes the disadvantages of the prior art. Likewise, a preparation process for cosmetic or dermatological preparations which comprise temperature-sensitive ingredients, as shown in FIG. 2 and characterized in that
(1) it is carried out continuously and
(2) by a sequence of the following process steps
(a) emulsification in mixing apparatuses (30), in combination with static mixers (28, 11) and/or homogenizers (29, 33),
(b) establishing a mixture temperature of 55-35° C. by adding (P,Q) aqueous phase of 15-50° C. with a lower temperature compared with the mixture,
(c) addition (R,S) of perfume oil and/or temperature-sensitive active ingredients at different temperatures,
(d) homogenization in apparatuses (29, 33) in the temperature range from either 50 to 80° C., particularly preferably 60 to 70° C. or 20 to 50° C., particularly preferably 28 to 45° C., very particularly preferably 30 to 40° C.,
(e) stepwise (stagewise) cooling during the process (32, 34), also remedies the disadvantages of the prior art. It is particularly preferred here when the entering preproducts have been heated beforehand to temperatures of from 40 to 100° C., particularly preferably 50 to 90° C.

DETAILED DESCRIPTION OF THE PREFERRED EMBODIMENTS

Figure 1:
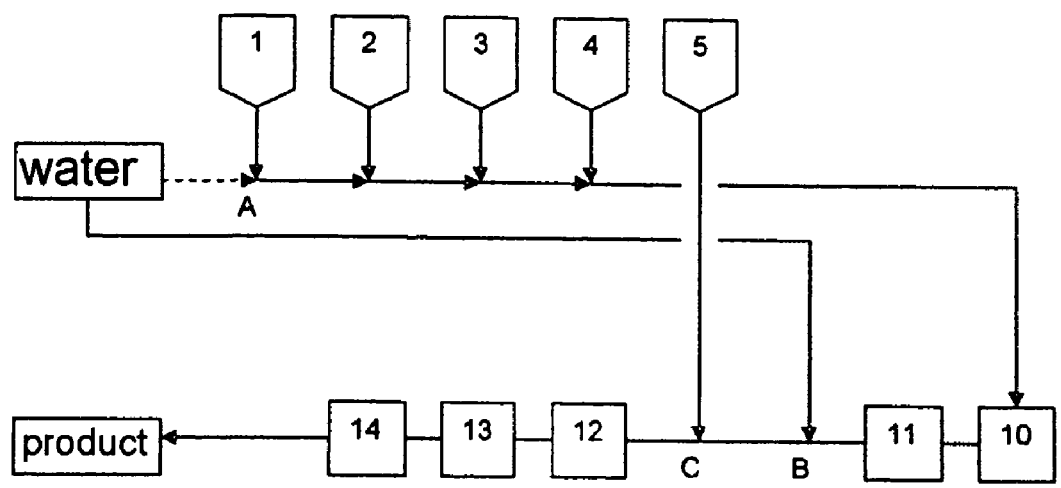
FIG. 1 is a schematic representation of one embodiment of the process of the present invention.
Figure 2:
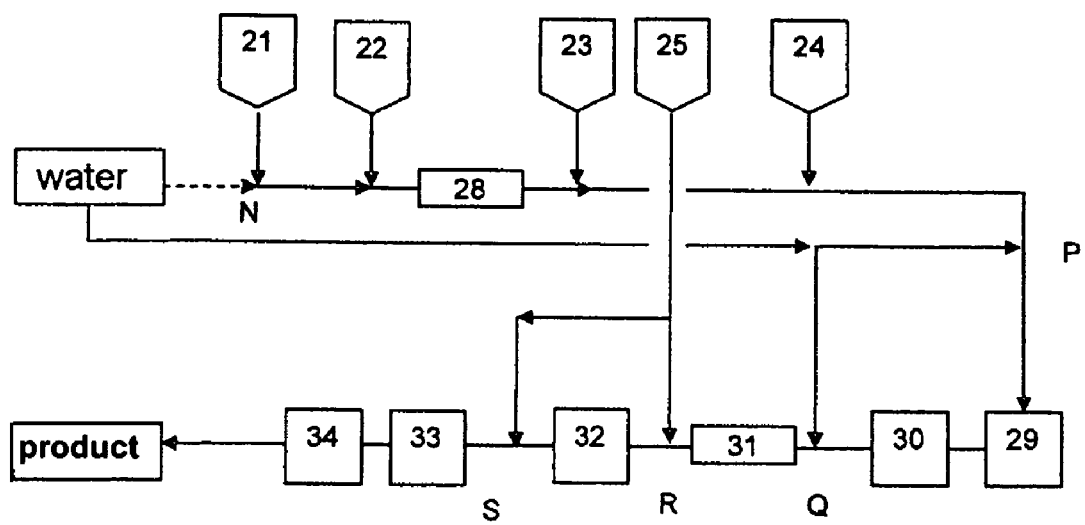
FIG. 2 is a schematic representation of another embodiment of the process of the present invention.

In this connection, it is preferred when, as a further downstream step (14), as shown in FIG. 1 or (32, 34), as shown in FIG. 2, the process product is cooled to at most 28 to 30° C. It is also preferred when the preproducts are mixed at temperatures of from 40 to 100° C., particularly preferably 50 to 90° C. before they enter the first mixing or homogenization apparatus. In addition, it is preferred when, upon passing through the homogenization apparatus (13), as shown in FIG. 1, the temperature of the exiting mixture increases 2 to 60° C., or upon passing through the homogenization apparatus (29, 33), as shown in FIG. 2, the temperature of the exiting mixture increases 2 to 10° C., based on the temperature of the entering mixture.

It is particularly preferred when the emulsification operation is carried out in two different mixing apparatuses (10) and (11), as shown in FIG. 1. It is very particularly preferred when the emulsification operation is carried out in a static mixer (10) and a loop mixer (11) (FIG. 1) or (29) and (33) (FIG. 2).

It is particularly preferred when the homogenization operation is carried out in a loop mixer (30) and a homogenizer (33), as shown in FIG. 2.

It is particularly preferred when the homogenization operation is carried out in two different apparatuses (12) and (13), as shown in FIG. 1. It is very particularly preferred when the homogenization operation is carried out in a static mixer (12) and a homogenizer (13).

It is very particularly preferred when the emulsification operation is carried out in a loop mixer (30) in combination with one or more homogenizers (29, 33), and static mixers (28, 31), as shown in FIG. 2.

The invention also covers emulsions, PIT emulsions and products comprising washing-active substances, obtainable by a process according to at least one of the variants described. Preferably, such emulsions, PIT emulsions and products comprising washing-active substances comprise, or are used in such processes as, temperature-sensitive ingredients, such as fragrances, vitamins, coenzymes, peptides, enzymes, nucleic acids, plant extracts, preservatives.

Through the process according to the invention it is possible to achieve particularly high throughput capacities of the plants used: to date, the capacity limits of customary plants were 3 t/h, whereas with the plant according to the invention up to 10 t/h can be achieved. In this regard, the process is very universally suitable for completely different types of product groups: besides W/O and O/W emulsions, PIT emulsions and products comprising washing-active substances can also be prepared in a particularly cost-effective manner on one and the same plant, the products being particularly stable and also storable over long periods. In view of the universal applicability of the plant, production may be at particularly low cost. In the case of PIT emulsions, particularly small droplet sizes can be achieved which can otherwise only be prepared in long-term storage-stable form in laboratory experiments.

This is of great advantage particularly when sunscreen formulations based on PIT emulsions are to be prepared: in this way, it is possible to incorporate a particularly large amount of photoprotective agent and thus achieve particularly high sun protection factors of up to 40 and above.

It is advantageous in the process according to the invention to use as loop mixer an apparatus which is characterized by a product feed arranged at a distance from the product discharge, a conveying device such as a multi-threaded conveying screw, which is located in an internal guide tube, the mixing of the product being effected as a result of the volume conveyed through the internal conveying device being a multiple of the volume introduced through the feed, giving rise to forced circulation outside the guide tube against the conveyance direction within the guide tube. It is particularly preferred to use a mixer of the Burdosa DMT 320 model. Such mixers have hitherto been used to prepare orange juice concentrate, yoghurt, salad sauces or other foods and allow the process parameters to be matched in a very variable manner to the requirements. For example, besides a pure mixer operation, emulsification or foaming are also possible.

It is advantageous in the process according to the invention to use as further mixer an apparatus which acts at the same time as a homogenizer. A homogenizer of the Becomix DH 500 model, Berents, Stuhr, Germany is preferably used. It is particularly advantageous to use a high-pressure homogenizer consisting of a high-pressure pump, a structured packing and a valve, as is described, for example, in European patent application 810025.

It is further advantageous, instead of the mixer (10), to use a combination of two mixing apparatuses, in particular a static mixer and a dynamic mixer. In this case, the temperature of the exiting mixture increases on passing through the combination of mixing apparatuses by 2 to 60° C., based on the temperature of the entering mixture.

As a result of high-pressure homogenization, heating in a separate process step is particularly advantageously superfluous since, as a result of the input of energy for the homogenization, the homogenized material is very effectively heated simultaneously.

A further advantage of the process according to the invention is the property that it is very easy to clean the plant when changing the product. A cleaning solution is fed in and circulated in a suitable manner, thus dispensing with dismantling or laborious cleaning in some other way. Such apparatuses are also referred to as cip-capable (clean in process).

The examples below are intended to illustrate the present invention without limiting it. The numerical values in the examples are percentages by weight, based on the total weight of the particular preparations.

EXAMPLES

Examples (1) to (5) relate to FIG. 1, and Examples (6) to (10) relate to FIG. 2. In FIG. 2, 28=static mixer, 29=Beco homogenizer, 30=loop mixer, 31=static mixer, 32=heat exchanger, 33=Beco homogenizer, 34=heat exchanger (1) Preparation of a Cream Containing Active Ingredient

| Container 2 | 44.168 | Demineralized water |
| | 7.500 | Glycerol |
| | 0.200 | Sodium hydroxide solution 45% |
| Container 1 | 3.000 | Glyceryl stearate citrate |
| | 2.000 | Caprylic/capric triglyceride |
| | 2.000 | Tridecyl stearate |
| | 1.100 | Stearyl alcohol |
| | 1.100 | Cetyl alcohol |
| | 1.500 | Hydrogenated coconut fatty glycerides |
| | 0.010 | Ceramide 3 |
| Cold water | 20.270 | Demineralized water |
| Container 4 | 3.000 | Dicaprylyl ether |
| | 0.400 | Carbomer |
| Container 3 | 0.002 | Ubiquinone |
| | 10.000 | Cyclomethicone |
| Container 5 | 3.000 | Ethanol |
| | 0.500 | Preservatives |
| | 0.250 | Perfume |

Firstly, the following phases are introduced into mixing containers: in mixing container (1) an oil phase heated to 60 to 95° C., in mixing container (2) a water phase heated to 80° C., in mixing container (3) an electrolyte-containing phase, in mixing container (4) a carbomer phase and in mixing container (5) a phase comprising perfume oil and active ingredients. Metering from the mixing containers is continuous. The oil phase from mixing container (1) is firstly combined with the water phase from mixing container (2), then the active-ingredient-containing phase from mixing container (3) and the carbomer phase from mixing container (4) are added. The mixture passes through a static inline mixer (10) model MS2G, Bran+Luebbe and is then emulsified in a loop mixer (11) model Burdosa DMT 320 at 500 revolutions per minute. The exiting emulsion has a temperature of 53.1° C., is cooled suddenly to 35-38° C. at point (B) with cold water, and the phase comprising perfume oil and active ingredients is added from mixing container (5) at point (C). After passing through a further static mixer (12), model MS2G Bran+Luebbe, the emulsion is homogenized in a homogenizer (13) model Becomix DH 500, Berents, where the temperature increases by 2 to 10° C. Cooling to 30° C. then takes place via heat exchanger (14) and the product is drawn off. A throughput of 2 t/h is achieved.

(2) Preparation of a Soft Cream

| Container 1 | 1.500 | Paraffin oil |
| | 2.500 | Stearic acid |
| | 2.000 | Petrolatum |
| | 3.500 | Myristyl alcohol |
| | 1.500 | Myristyl myristate |
| | 1.200 | Glyceryl stearate |
| | 1.000 | Hydrogenated coconut fatty glycerides |
| | 0.100 | Cetyl phosphate |
| | 0.350 | Preservatives |
| Container 2 | 23.630 | Demineralized water |
| | 3.500 | Glycerol |
| Container 3 | 4.800 | Demineralized water |
| | 0.600 | Sodium hydroxide solution 45% |
| Container 4 | 0.750 | Dimethicone |
| | 0.300 | Carbomer |
| | 18.750 | Demineralized water |
| | 2.800 | Ethanol, denatured |
| Container 5 | 0.500 | Tocopheryl acetate |
| | 0.350 | Polyglyceryl-2 caprate |
| | 0.200 | Ethanol |
| | 0.170 | Perfume |
| Cold water | 30.000 | Demineralized water |

Firstly, the following phases are introduced into mixing containers: in mixing container (1) an oil phase heated to 60 to 95° C., in mixing container (2) a water phase heated to 80° C., in mixing container (3) an NaOH-containing phase, in mixing container (4) a carbomer phase and in mixing container (5) a phase comprising perfume oil and active ingredients. Metering from the mixing containers is continuous. The oil phase from mixing container (1) is firstly combined with the water phase from mixing container (2), then the water phase from mixing container (2), NaOH-containing phase from mixing container (3) and the carbomer phase from mixing container (4) are added. The mixture passes through a static inline mixer (10) model MS2G, Bran+Luebbe and is then emulsified in a loop mixer (11) model Burdosa DMT 320 at 1400 revolutions per minute. During this, the temperature increases to 46.3° C. The exiting emulsion is cooled suddenly to 31.1° C. at point (B) with cold water, and the phase comprising perfume oil and active ingredients is added from mixing container (5) at point (C). After passing through a further static mixer (12), model MS2G Bran+Luebbe, the emulsion is homogenized in the homogenizer (13) model Becomix DH 500, Berents, where the temperature increases to 46.9° C. Cooling to 30° C. is then carried out via heat exchanger (14) and the product is drawn off. A throughput of 3.2 t/h is achieved.

(3) Preparation of a Skincare Liquid Soap

| Container 1 | 3.000 | Cocoamidopropylbetaine |
| | 0.500 | Citric acid |
| | 0.300 | PEG-40 hydrogenated castor oil |

| | | -continued |
|---|---|---|
| Container 2 | 7.000 | Demineralized water |
| | 1.000 | Trisodium EDTA 20% strength solution |
| | 0.500 | Acrylate copolymer |
| | 0.450 | Sodium benzoate |
| | 0.800 | PEG-200 hydrogenated glyceryl palm oil fatty acid ester |
| | 4.000 | Disodium coconut fatty acid glutamate |
| Container 3 | 6.101 | Demineralized water |
| | 2.000 | Sodium chloride |
| Container 4 | 25.000 | Sodium laureth sulphate |
| Container 5 | 4.350 | Cocoamidopropylbetaine |
| | 0.300 | Perfume |
| | 2.000 | Decyl polyglucose |
| Cold water | 6.000 | Demineralized water |
| | 2.000 | Sodium chloride |

Firstly, the following phases are introduced into mixing containers: in mixing container (1) an oil phase heated to 40° C., in mixing container (2) a water phase heated to 40° C., in mixing container (3) an electrolyte-containing phase, in mixing container (4) liquid lauryl ether sulphate and in mixing container (5) a phase comprising perfume oil and active ingredients. Metering from the mixing containers is continuous. The oil phase from mixing container (1) is firstly combined with the water phase from mixing container (2), then the water phase from mixing container (2), electrolyte-containing phase from mixing container (3) and the liquid lauryl ether sulphate from mixing container (4) are added. The mixture passes through a static inline mixer (10) model MS2G, Bran+Luebbe and is then emulsified in a loop mixer (11) model Burdosa DMT 320 at 150 revolutions per minute. During this, the temperature increases to 22.2° C. The exiting emulsion is cooled suddenly to 18° C. at point (C) with cold water, and the phase comprising perfume oil and active ingredients is added from mixing container (5) at point (C). After passing through a further static mixer (12), model MS2G, Bran+Luebbe, the washing-active product is homogenized in a homogenizer (13) model Becomix DH 500, Berents, where the temperature increases to 20.9° C. The product is then drawn off. A throughput of 2.5 t/h is achieved.

(4) Preparation of a Sunscreen Spray (PIT Emulsion)

| | | |
|---|---|---|
| Container 1 | 5.400 | Glyceryl stearate + ceteareth-20 + ceteareth-12 + cetearyl alcohol |
| | 3.000 | Tridecyl stearate (+) tridecyl trimellitate |
| | 3.300 | C12-C15 alkyl benzoate |
| | 0.500 | PVP/hexadecene copolymer |
| | 5.000 | Octyl methoxycinnamate |
| | 2.600 | Ceteareth-20 |
| | 2.000 | Octyltriazone |
| | 1.000 | Diethylhexylbutamidotriazone |
| | 1.000 | Dicaprylyl ether |
| Container 2 | 32.15 | Demineralized water |
| | 5.000 | Glycerol |
| Container 3 | 7.800 | Demineralized water |
| | 0.150 | Sodium hydroxide solution 45% |
| | 0.500 | Phenylbenzimidazolesulphonic acid |
| Container 4 | 2.000 | Demineralized water |
| | 0.400 | DMDM hydantoin |
| Container 5 | 0.400 | Preservatives |
| | 0.500 | Tocopheryl acetate |
| | 0.300 | Perfume |
| Cold water | 27.000 | Demineralized water |

Firstly, the following phases are introduced into mixing containers: in mixing container (1) an oil phase heated to 60 to 95° C., in mixing container (2) a water phase heated to 60 to 95° C., in mixing container (3) an electrolyte-containing phase, in mixing container (4) a preservative phase and in mixing container (5) a phase comprising perfume oil and active ingredients. Metering from the mixing containers is continuous. The oil phase from mixing container (1) is firstly combined with the water phase from mixing container (2), then the water phase from mixing container (2), electrolyte-containing phase from mixing container (3) and the preservative phase from mixing container (4) are added. The mixture passes through a static inline mixer (10) model MS2G, Bran+Luebbe and is then emulsified in a loop mixer (11) model Burdosa DMT 320 at 1000 revolutions per minute. The exiting emulsion has a temperature of 93.1° C., is cooled suddenly to 61.2° C. at point (B) with cold water, and the phase comprising perfume oil and active ingredients from mixing container (5) is added at point (C). After passing through a further static mixer (12), model MS2G, Bran+Luebbe, the emulsion is homogenized in a homogenizer (13) model Becomix DH 500, Berents, where the temperature increases by 2 to 10° C. Cooling to 28.6° C. is then carried out by heat exchanger (14) and the product is drawn off. The product has a droplet size of 103.5 nm. A throughput of 3.5 t/h is achieved.

(5) Preparation of a Sun Milk

| | | |
|---|---|---|
| Container 1 | 5.500 | C12-C15 alkyl benzoate |
| | 4.160 | Glyceryl stearate self-emulsifying |
| | 2.500 | Caprylic/capric triglyceride |
| | 2.240 | Stearic acid |
| | 0.750 | Cetearyl ether |
| | 3.000 | Octyltriazone |
| | 2.500 | Tocopheryl acetate |
| | 5.500 | Octyl methoxycinnamate |
| | 1.000 | Titanium dioxide |
| Container 2 | 14.806 | Demineralized water |
| | 7.500 | Glycerol |
| | 2.500 | Butylene glycol |
| | 0.044 | Sodium hydroxide solution 45% |
| Container 3 | 19.300 | Demineralized water |
| | 2.000 | Dicaprylyl ether |
| | 0.500 | Xanthan gum |
| Container 5 | 3.500 | Ethanol |
| | 0.300 | Preservatives |
| | 2.000 | Capryl/capric triglyceride |
| | 0.400 | Perfume |
| Cold water | 20.000 | Demineralized water |

Firstly, the following phases are introduced into mixing containers: in mixing container (1) an oil phase heated to 60 to 95° C., in mixing container (2) a water phase heated to 80° C., in mixing container (3) a thickener phase and in mixing container (5) a phase comprising perfume oil and active ingredients. Metering from the mixing containers is continuous. The oil phase from mixing container (1) is firstly combined with the water phase from mixing container (2), then the water phase from mixing container (2), and the thickener phase from mixing container (3) are added. The mixture passes through a static inline mixer (10) model MS2G, Bran+Luebbe and is then emulsified in a loop mixer (11) model Burdosa DMT 320 at 1000 revolutions per minute. The exiting emulsion has a temperature of 46.2° C., is cooled suddenly to 35-38° C. at point (B) with cold water, and the phase comprising perfume oil and active ingredients from mixing container (5) is added at point (C). After passing through a further static mixer (12), model MS2G Bran+Luebbe, the emulsion is homogenized in a homogenizer (13) model Becomix DH 500, Berents, where the temperature increases by 7 to 11° C. Cooling to 30° C. is then carried out by heat exchanger (14) and the product is drawn off. A throughput of 2 t/h is achieved.

(6) Preparation of a Cream Containing Active Ingredient

| | | |
|---|---|---|
| Container 2 | 45.178 | Demineralized water |
| | 7.500 | Glycerol |
| | 0.200 | Sodium hydroxide solution 45% |
| Container 1 | 3.000 | Glyceryl stearate citrate |
| | 4.000 | Caprylic/capric triglyceride |
| | 2.600 | Cetyl alcohol |
| Cold water | 20.270 | Demineralized water |
| Container 4 | 3.000 | Dicaprylyl ether |
| | 0.400 | Carbomer |
| Container 3 | 0.002 | Active ingredients |
| | 10.000 | Cyclomethicone |
| Container 5 | 3.100 | Ethanol |
| | 0.500 | Preservatives |
| | 0.250 | Perfume |

Firstly, the following phases are introduced into mixing containers: in mixing container (21) an oil phase heated to 60 to 95° C., in mixing container (22) a water phase heated to 60 to 80° C., in mixing container (23) an electrolyte-containing phase, in mixing container (24) a carbomer phase and in mixing container (25) a phase comprising perfume oil and active ingredients. Metering from the mixing containers is continuous. The oil phase from mixing container (21) is firstly combined with the water phase from mixing container (22), and passes through a static inline mixer (28) model MS2G, Bran+Luebbe, then the active-ingredient-containing phase from mixing container (23) and the carbomer phase from mixing container (24) are added. The mixture passes through the homogenizer model Becomix DH 500, Berents (29) with 800 revolutions per minute and is then emulsified in a loop mixer (30) model Burdosa DMT 320 at 500 revolutions per minute. The exiting emulsion has a temperature of 53.1° C., is cooled suddenly to 35-38° C. at point (Q) with cold water. After passing through a further static mixer (31), model MS2G, Bran+Luebbe and cooling to 31° C. in the heat exchanger (32), the phase comprising perfume oil and active ingredients from mixing container (25) is added at point (S). The emulsion is then homogenized in a homogenizer (33) model Becomix DH 500, Berents, with 2000 revolutions per minute, where the temperature increases by 2 to 10° C. Cooling to 28° C. is then carried out by heat exchanger (34) and the product is drawn off. A throughput of 6 t/h is achieved.

(7) Preparation of a Soft Cream

| | | |
|---|---|---|
| Container 1 | 3.500 | Paraffin oil |
| | 1.500 | Stearic acid |
| | 0.500 | Myristyl myristate |
| | 1.100 | Hydrogenated coconut fatty glycerides |
| | 0.350 | Preservatives |
| Container 2 | 29.130 | Demineralized water |
| | 3.500 | Glycerol |
| Container 3 | 6.000 | Demineralized water |
| | 0.600 | Sodium hydroxide solution 45% |
| Container 4 | 0.750 | Dimethicone |
| | 0.300 | Carbomer |
| | 18.750 | Demineralized water |
| | 2.800 | Ethanol, denatured |
| Container 5 | 0.500 | Actives |
| | 0.350 | Silicone oil |
| | 0.200 | Ethanol |
| | 0.170 | Perfume |
| Cold water | 30.000 | Demineralized water |

Firstly, the following phases are introduced into mixing containers: in mixing container (21), an oil phase heated to 60 to 95° C., in mixing container (22) a water phase heated to 80° C., in mixing container (23) an NaOH-containing phase, in mixing container (24) a carbomer phase and in mixing container (25) a phase comprising perfume oil and active ingredients. Metering from the mixing containers is continuous.

The oil phase from mixing container (21) is firstly combined with the water phase from mixing container (22), and passes through a static inline mixer (28) model MS2G, Bran+Luebbe, then the NaOH-containing phase from mixing container (23) and the carbomer phase from mixing container (24) are added. Shortly before the homogenizer (29) model Becomix DH 500, Berents, cooling is carried out suddenly to 38-41° C. at point (P) with cold water. The mixture passes through the homogenizer model Becomix DH 500, Berents at 1000 revolutions (29) and is then emulsified in a loop mixer (30) model Burdosa DMT 320 at 1400 revolutions per minute. During this, a temperature of 42.3° C. Is established. After passing through a further static mixer (31), model MS2G, Bran+Luebbe and cooling in heat exchanger (32), the phase comprising perfume oil and active ingredients from mixing container (25) is added at point (R). The emulsion is then homogenized in an homogenizer (33) model Becomix DH 500, Berents, with 1000 revolutions per minute, where the temperature increases by 2 to 10° C. Cooling to 30° C. is then carried out by heat exchanger (34), and the product is drawn off. A throughput of 6 t/h is achieved.

(8) Preparation of a Skincare Liquid Soap

| | | |
|---|---|---|
| Container 1 | 3.500 | Cocoamidopropylbetaine |
| | 0.300 | PEG-40 hydrogenated castor oil |
| Container 2 | 8.000 | Demineralized water |
| | 0.500 | Acrylate copolymer |
| | 0.450 | Preservatives |
| | 4.800 | Disodium coconut fatty acid glutamate |
| Container 3 | 6.101 | Demineralized water |
| | 2.000 | Sodium chloride |
| Container 4 | 25.000 | Sodium laureth sulphate |
| Container 5 | 6.350 | Cocamidopropylbetaine |
| | 0.300 | Perfume |
| Cold water | 40.699 | Demineralized water |

Firstly, the following phases are introduced into mixing containers: in mixing container (21) an oil phase heated to 40° C., in mixing container (22) a water phase heated to 40° C., in mixing container (23) an electrolyte-containing phase, in mixing container (24) liquid lauryl ether sulphate and in mixing container (25) a phase comprising perfume oil and active ingredients. Metering from the mixing containers is continuous. The oil phase from mixing container (21) is firstly combined with the water phase from mixing container (22) and passes through a static inline mixer (28) model MS2G, Bran+Luebbe, then the electrolyte-containing phase from mixing container (23) and liquid lauryl ether sulphate from mixing container (24) are added. The mixture passes through the homogenizer model Becomix DH 500, Berents (29) at just 500 revolutions per minute and is then mixed intensively in a loop mixer (30) model Burdosa DMT 320 at 1000 revolutions per minute. During this, the temperature increases to 22.2° C. The exiting emulsion is cooled suddenly to 18° C. at point (Q) with cold water, and the phase comprising perfume oil and active ingredients from mixing container (25) is added at point (R). After passing through a further static mixer (31), model MS2G, Bran+Luebbe, the phase comprising perfume oil and active ingredients from mixing container (25) is added at point (S). The heat exchangers (32, 34) have no function here. Finally, the washing-active product is homogenized in a homogenizer (33) model Becomix DH 500, Berents, with 1000 revolutions per minute, where the temperature increases to 20.9° C. The product is then drawn off. A throughput of 8 t/h is achieved.

(9) Preparation of a Sunscreen Spray (PIT Emulsion)

| Container 1 | 5.400 | Glyceryl stearate + Ceteareth-20 + Ceteareth-12 + cetearyl alcohol |
| | 3.000 | Tridecyl stearate (+) tridecyl trimellitate |
| | 3.300 | C12-15 alkyl benzoate |
| | 3.100 | Paraffin oil |
| | 7.000 | Octyl methoxycinnamate |
| | 1.000 | Diethylhexylbutamidotriazone |
| Container 2 | 33.15 | Demineralized water |
| | 5.000 | Glycerol |
| Container 3 | 7.800 | Demineralized water |
| | 0.150 | Sodium hydroxide solution 45% |
| | 0.500 | Phenylbenzimidazolesulphonic acid |
| Container 4 | 2.000 | Demineralized water |
| | 0.400 | Preservatives |
| Container 5 | 0.400 | Preservatives |
| | 0.500 | Active ingredients |
| | 0.300 | Perfume |
| Cold water | 27.000 | Demineralized water |

Firstly, the following phases are introduced into mixing containers: in mixing container (21) an oil phase heated to 60 to 95° C., in mixing container (22) a water phase heated to 60 to 95° C., in mixing container (23) an electrolyte-containing phase, in mixing container (24) a preservative phase and in mixing container (25) a phase comprising perfume oil and active ingredients. Metering from the mixing containers is continuous. The oil phase from mixing container (21) is firstly combined with the water phase from mixing container (22), and passes through a static inline mixer (28) model MS2G, Bran+Luebbe, then the electrolyte-containing phase from mixing container (23) and preservative phase from mixing container (24) are added. The mixture passes through the homogenizer model Becomix DH 500, Berents (29), although it is switched off for this type of emulsion. The emulsion is then emulsified in a loop mixer (31) model Burdosa DMT 320 at 1000 revolutions per minute. The exiting emulsion has a temperature of 93.1° C. and is cooled suddenly to 61.2° C. at point (Q) with cold water. The mixture passes through a static inline mixer (30) model MS2G, Bran+Luebbe and then the phase comprising perfume oil and active ingredients from mixing container (25) is added at point (R). After passing through a heat exchanger (32), where the temperature adjusts to 38° C., the emulsion is homogenized in a homogenizer (33) model Becomix DH 500, Berents, at 500 revolutions per minute, during which the temperature does not increase. Cooling to 28.6° C. is then carried out by heat exchanger (34) and the product is drawn off. The product has a particle size of 103.5 nm. A throughput of 7 t/h is achieved.

(10) Preparation of a Sun Milk

| Container 1 | 8.500 | Paraffin oil |
| | 4.160 | Glyceryl stearate self-emulsifying |
| | 2.500 | Caprylic/capric triglyceride |
| | 2.240 | Stearic acid |
| | 0.750 | Cetearyl alcohol |
| | 2.500 | Active ingredients |
| | 5.500 | Octyl methoxycinnamate |
| | 1.000 | Titanium dioxide |
| Container 2 | 22.306 | Demineralized water |
| | 2.500 | Butylene glycol |
| | 0.044 | Sodium hydroxide solution 45% |
| Container 3 | 19.300 | Demineralized water |
| | 2.000 | Dicaprylyl ether |
| | 0.500 | Xanthan gum |

-continued

| Container 5 | 3.500 | Ethanol |
| | 0.300 | Preservatives |
| | 2.000 | Caprylic/capric triglyceride |
| | 0.400 | Perfume |
| Cold water | 20.000 | Demineralized water |

Firstly, the following phases are introduced into mixing containers: in mixing container (21) an oil phase heated to 60 to 95° C., in mixing container (22) a water phase heated to 60 to 80° C., in mixing container (23) a thickener phase and in mixing container (25) a phase comprising perfume oil and active ingredients. Metering from the mixing containers is continuous. The oil phase from mixing container (21) is firstly combined with the water phase from mixing container (22) and passes through a static inline mixer (28) model MS2G, Bran+Luebbe, then the thickener phase from mixing container (23) is added. The mixture passes through the homogenizer model Becomix DH 500, Berents with 1200 revolutions per minute (29) and is then emulsified in a loop mixer (30) model Burdosa DMT 320 at 1200 revolutions per minute. The exiting emulsion has a temperature of 46.2° C. and is cooled suddenly to 35-38° C. at point (Q) with cold water. After passing through a further static mixer (31), model MS2G, Bran+Luebbe and cooling in the heat exchanger (32), the phase comprising perfume oil and active ingredients from mixing container (25) is added at point (S). The emulsion is then homogenized in a homogenizer (13) model Becomix DH 500, Berents, at 2000 revolutions per minute, during which the temperature increases by 2 to 10° C. Cooling to 30° C. is then carried out by heat exchanger (14) and the product is drawn off. A throughput of 6 t/h is achieved.

That which is claimed:

1. A process for preparing a cosmetic or dermatological preparation, wherein the process is continuous and comprises:
    (a) emulsifying at least two pre-products in at least one mixing device to form an emulsion,
    (b) adding to the emulsion of (a) water or an aqueous solution having a temperature which is lower than the temperature of the emulsion to form a cooled emulsion having a temperature of less than 40° C.,
    (c) adding to the cooled emulsion at least one substance selected from perfume oils and temperature-sensitive active ingredients, and
    (d) homogenizing the cooled emulsion and the at least one substance in at least one homogenizing device at a temperature of from 20° C. to 50° C. to form a homogenized emulsion.

2. The process of claim 1, further comprising: (e) cooling the homogenized emulsion of (d) to a temperature of less than 30° C.

3. The process of claim 1, wherein in (a) the pre-products are mixed at a temperature of from 40° C. to 100° C. prior to entering said at least one mixing device.

4. The process of claim 1, wherein the temperature of the homogenized emulsion of (d) is greater than the temperature of the combined cooled emulsion and the at least one substance by from 2° C. to 60° C.

5. The process of claim 1, wherein (a) is carried out in two different mixing devices.

6. The process of claim 5, wherein (a) is carried out in a static mixer and a loop mixer.

7. The process of claim 1, wherein (d) is carried out in two different devices.

8. The process of claim 7, wherein (d) is carried out in a static mixer and a homogenizer.

9. The process of claim 1, wherein the at least one substance comprises at least one temperature sensitive active ingredient.

10. The process of claim 9, wherein the at least one temperature-sensitive active ingredient comprises at least one ingredient selected from fragrances, vitamins, coenzymes, peptides, enzymes, nucleic acids, plant extracts and preservatives.

11. A process for preparing a cosmetic or dermatological preparation, wherein the process is continuous and comprises:
(a) emulsifying at least two pre-products in at least one mixing device in combination with one or more of at least one static mixer and at least one homogenizer to form an emulsion,
(b) adding to the emulsion water or an aqueous solution having a temperature of from 15° C. to 50° C. to form a cooled emulsion having a temperature of from 35° C. to 55° C.,
(c) adding to the cooled emulsion of (b) at least one substance selected from perfume oils and temperature-sensitive active ingredients, and
(d) homogenizing the cooled emulsion and the at least one substance at a temperature of from 20° C. to 80° C. to form a homogenized emulsion,
and wherein the process comprises stepwise cooling during the process.

12. The process of claim 11, wherein prior to emulsification in (a) the at least two pre-products are heated to a temperature of from 40° C. to 100° C.

13. The process of claim 12, wherein prior to emulsification the at least two pre-products are heated to a temperature of from 50° C. to 90° C.

14. The process of claim 11, wherein in (d) homogenizing the cooled emulsion and the at least one substance is carried out at a temperature of from 20° C. to 50° C.

15. The process of claim 11, wherein in (d) homogenizing the cooled emulsion and the at least one substance is carried out at a temperature of from 28° C. to 45° C.

16. The process of claim 11, wherein in (d) homogenizing the cooled emulsion and the at least one substance is carried out at a temperature of from 30° C. to 40° C.

17. The process of claim 11, wherein in (d) homogenizing the cooled emulsion and the at least one substance is carried out at a temperature of from 60° C. to 70° C.

18. The process of claim 11, wherein (d) is carried out in a loop mixer and a homogenizer.

19. The process of claim 11, wherein (c) is carried out in a loop mixer in combination with at least one homogenizer and at least one static mixer.

20. The process as claimed in claim 11, wherein the at least one substance comprises at least one temperature-sensitive active ingredient.

21. The process of claim 20, wherein the at least one temperature-sensitive active ingredient comprises at least one ingredient selected from fragrances, vitamins, coenzymes, peptides, enzymes, nucleic acids, plant extracts and preservatives.

22. The process of claim 1, wherein the cosmetic or dermatological preparation comprises a PIT emulsion.

23. The process of claim 11, wherein the cosmetic or dermatological preparation comprises a PIT emulsion.

24. The process of claim 1, wherein the process is carried out at a throughput of higher than 3 t/h.

25. The process of claim 11, wherein the process is carried out at a throughput of higher than 3 t/h.

* * * * *